United States Patent [19]

McClintock, II

[11] Patent Number: 5,573,399
[45] Date of Patent: Nov. 12, 1996

[54] APPLICATION FOR APPLYING A BLEACHING AGENT TO TEETH AND METHOD THEREFOR

[76] Inventor: Robert A. McClintock, II, 6525 Esplanade St., Playa Del Rey, Calif. 90293

[21] Appl. No.: 327,977

[22] Filed: Oct. 24, 1994

[51] Int. Cl.$^6$ .............................. A61G 17/02; A61G 5/00; A61G 9/00
[52] U.S. Cl. ................... 433/80; 433/41; 433/215
[58] Field of Search ................... 433/6, 37, 41, 433/42, 43, 71, 80, 214, 215, 216; 121/859, 860, 861

[56] References Cited

U.S. PATENT DOCUMENTS

| | | | |
|---|---|---|---|
| 1,378,297 | 5/1921 | Wallace | 433/47 |
| 1,606,069 | 11/1926 | Freedman et al. | 433/47 |
| 1,608,632 | 11/1926 | Strusser | 433/41 |
| 2,963,786 | 12/1960 | Browning | 433/37 |
| 3,955,281 | 5/1976 | Weitzman | 128/861 X |
| 3,978,585 | 9/1976 | Holcomb | 433/41 |
| 4,063,552 | 12/1977 | Going et al. | 128/861 |
| 4,368,040 | 1/1983 | Weissman | 433/41 X |
| 4,968,251 | 11/1990 | Darnell | 433/80 X |
| 4,983,380 | 1/1991 | Yarborough | 433/215 X |
| 4,990,089 | 2/1991 | Munro | 433/215 |
| 5,037,295 | 8/1991 | Bergersen | 433/6 |
| 5,165,424 | 11/1992 | Silverman | 128/861 |

Primary Examiner—Nicholas D. Lucchesi
Attorney, Agent, or Firm—Robert J. Schaap

[57] ABSTRACT

An applicator for applying a bleaching agent in the form of a bleaching gel composition to the teeth of a user for purposes of whitening or brightening the teeth. The applicator is in the form of an arch or so-called "tray". The applicator is formed of a flexible and bendable plastic, such as a vinyl plastic, so as to be capable of being partially molded to conform to the teeth configuration of a user. A spacer or insert is located in the tray and contacts the front surfaces of the teeth when inserted on the teeth. The spacer is spaced slightly rearwardly from the front surface of the arch-shaped tray to create a reservoir when the tray is effectively molded to conform to the configuration of the user's teeth. The user of the applicator inserts the applicator into his or her mouth after heating the applicator and the insert and which causes the plastic to become somewhat moldable. In the heated stage, the applicator, with the insert or spacer located therein, will essentially mold and conform to the shape and contour of the user's teeth. When the applicator is removed from the user's mouth and when the insert is removed from the tray, a reservoir will exist in the frontal portion of the tray, so as to receive and retentively hold the bleaching gel composition against the front surface of the teeth.

29 Claims, 2 Drawing Sheets

APPLICATION FOR APPLYING A BLEACHING AGENT TO TEETH AND METHOD THEREFOR

BACKGROUND OF THE INVENTION

1. Field of the Invention

This invention relates in general to certain new and useful improvements in applicators for applying a bleaching composition to the teeth of a user and a method of use therefor, and more particularly, to an applicator and associated method which permits an effective molding of a tray to the teeth configuration and the arch of a user without intervening professional assistance and laboratory participation.

2. Brief Description of the Related Art

In dental cosmetics, the whitening of teeth and particularly, those teeth which are exposed in a smiling zone, has become a very prominent activity. Generally, yellow-colored or non-white colored teeth, and particularly teeth which have color variation from tooth to tooth are relatively unattractive and moreover, detracts from the smile of an individual or when the individual is conversing. Thus, white teeth, and particular, uniformly white teeth are fashionable, if not necessary, for key persons in the entertainment industry and for others who work with the public in general.

Generally, the whitening of teeth usually relies upon the application of an oxidizing gel, such as a peroxide-containing gel, e.g., carbamide peroxide. This peroxide-containing gel is disposed against the teeth for a period of time, usually on a repeated basis, one or more hours per day for several days in succession until the teeth actually bleach by virtue of the peroxide-containing gel. However, some means must be provided to hold the gel against the teeth and to preclude the gel from dropping on the tongue or against the gums or being swallowed.

There are two commonly used approaches in the bleaching of teeth. The first approach is a home remedy or so-called "over-the-counter" remedy in which the user purchases a tray designed to fit around a portion of the arch containing those teeth in the smiling zone along with a peroxide-containing gel. In this way, the home user can place the gel on the tray and place the tray on the arch of teeth which are to be bleached. This approach has many serious disadvantages. The tray, while being somewhat flexible, is clearly not contoured to conform to the arch contour and the teeth contour of the user. The so-called "one size fits all" type of tray is obviously ineffective to accommodate a differing size arch, and particularly differing arch configurations. It is virtually impossible to make one tray accommodate numerously sized arches in close-fitting contact.

Due to the fact that this one size tray is not designed to be contoured to the particular arch of an individual, the gel is not consistently held against the teeth. Moreover, the gel is not uniformly held against the teeth. As a result, some teeth will bleach more than others, creating an uneven bleaching pattern which may be more undesirable than the original condition. In addition to the foregoing, health concerns can arise where the peroxide-containing gel should leak from the tray into a user's mouth.

The peroxide-containing gel which does not remain in the tray has a taste which is relatively unpalatable to many users. Even more so, and while the peroxide does not have a serious gastrointestinal effect, many of the persons using this approach have limited tolerance for the gel. As a result, they suffer indigestion and other problems if the gel is swallowed.

A peroxide-containing gel can also be an irritant to those persons having sensitive gums and mouth tissue, particularly if those persons have experienced previous gingival diseases.

In addition to the foregoing, compliance is another problem which often leads to unsatisfactory results. It is oftentimes necessary to apply this peroxide-containing gel on a daily basis for a selected period of time as, for example, several weeks. Due to the fact that many users will apply the gel on a somewhat intermittent basis, the results are oftentimes less than effective. Another approach which is more effective than the home use approach is that of having a professional dental practitioner apply the gel on a periodic basis. In this case, a metal dental tray is used for making an alginate impression. After the alginate material, somewhat similar to a plaster of paris material, is poured into the tray and the tray held against the patient's arch of teeth, an impression or mold is produced. Thereafter, a plastic material is carefully placed over the teeth to effectively oversize the surface of the teeth. Finally, a plastic sheet is then disposed around the mold with the plastic material thereon in order to create a tray. When the plastic sheet is heated, it will tightly adhere around the mold and thereby adopt the shape of the mold with a plastic filler. Due to the fact that the filler is present, a slight void is created around each tooth due to the over sizing. This void is effective to receive the peroxide-containing gel and hold the gel against the teeth.

While the above-described method of using a dental practitioner is far more effective than the home remedy, it is also considerably more expensive due to the fact that the user requires the involvement of a dental practitioner. Moreover, considerable laboratory time and associated laboratory costs are involved. Further, there is the attendant inconvenience of the user having to visit the dental practitioner on several occasions.

OBJECTS OF THE INVENTION

It is, therefore, one of the primary objects of the present invention to provide an applicator for receiving and retaining a bleaching gel to be applied to the teeth of a user and which is uniquely designed so as to enable the gel to be held in a reservoir for disposition against the teeth of a user.

It is another object of the present invention to provide an applicator of the type stated which can be effectively molded to the teeth configuration and arch of a user with a reservoir formed therein for receiving a bleaching gel and which does not require professional assistance and laboratory intervention.

It is a further object of the present invention to provide an applicator of the type stated which is in the form of a tray capable of being molded by a user to conform to the user's arch and teeth configuration.

It is an additional object of the present invention to provide a system utilizing an applicator for effectively brightening or whitening the teeth of a user without the need for professional dental intervention.

It is also an object of the present invention to provide an applicator and a system utilizing this applicator which maintains patient compliance and teeth whitening or brightening at a relatively low cost.

It is another salient object of the present invention to provide a method of molding a tray to conform to the arch and teeth configuration of a user on a home-use basis and without professional dental intervention.

It is still another object of the present invention to provide a method of the type stated which allows a user to apply a bleaching gel to the user's teeth without any attendant danger of leaching of the gel from the tray into the mouth of the user.

With the above and other objects in view, my invention resides in the novel features and form, construction, arrangement and combination of components, as well as the combination of method steps described and claimed herein.

BRIEF SUMMARY OF THE INVENTION

The present invention relies upon the use of a unique tray designed for the holding of a peroxide-containing gel against the teeth of a user. The tray of the present invention can be used by an individual on a home-use or non-prescription basis. Moreover, it eliminates those problems which were inherent in the prior art trays used for the application of the peroxide-containing gel to the teeth of a user.

In accordance with the present invention, a plastic tray, and preferably a vinyl plastic tray, is provided. These vinyl trays are somewhat pliable and bendable so that they can be partially bent to conform to the shape of the mouth of a user. An insert or liner, also formed of a moldable vinyl plastic, is located in the tray so as to fit against the exterior surface of the teeth in the arch. The insert or liner bears against the frontal surface of the teeth in the arch and moreover, is slightly spaced rearwardly of the front wall of the tray. In this way, a slight space is formed between the insert and the interior wall surface of the tray.

When the vinyl tray, with the insert therein, is initially heated as, for example, in a bath of hot water, it is in a condition where the vinyl is soft and pliable and hence, can be molded. Thereafter, the tray is introduced into the user's mouth. While in the heated condition, the vinyl in the plastic tray, which is then somewhat moldable and pliable, will effectively conform to the shape and configuration of a user's mouth. In so doing, and due to the fact that a liner exists between the interior surface of the wall of the tray, a reservoir is formed when the liner is removed. After the tray has been effectively molded so as to conform to the shape of the user's arch, the tray is then inserted into a hot water bath or other means for heating the same and allowed to cool. The tray then constitutes an accurate reverse reproduction of the user's arch or so-called mold with a reservoir created therein spanning the frontal position of the tray.

In this way, when the tray is placed against the arch, the teeth will fit into the pre-formed tray with a slight cavity existing between the front surface of the teeth and the tray itself. This cavity constitutes a reservoir for the receipt of the gel to be placed against the front of each tooth in the arch. The same holds true for both the upper and the lower arch.

The liner is adapted for removable attachment to the interior surface of the tray by means of tabs or the like. However, any means for holding the liner in place in a removable fashion may be employed for this purpose.

In accordance with the system of the present invention, the tray is uniquely designed to not only fit the teeth configuration of the user without the need of an expensive mold, but it is also effective in holding the gel against the teeth of the user. In this way, the gel is precluded from dropping onto the tongue and into the oral cavity and even more so, it is not likely to be swallowed by the user. Thus, the home use tray accomplishes all of the advantages which would be achieved by having a mold prepared with a dental practitioner and at a fraction of the cost.

This invention possesses many other advantages and has other purposes which may be made more clearly apparent from a consideration of the forms in which it may be embodied. These forms are shown in the drawings forming a part of and accompanying the present specification. They will now be described in detail for purposes of illustrating the general principles of the invention, but it is to be understood that this detailed description and the accompanying drawings are not to be taken in a limiting sense.

DETAILED DESCRIPTION OF THE DRAWINGS

Having thus described the invention in general terms, reference will now be made to the accompanying drawings in which:

DETAILED DESCRIPTION OF PREFERRED EMBODIMENTS

Figure 1:
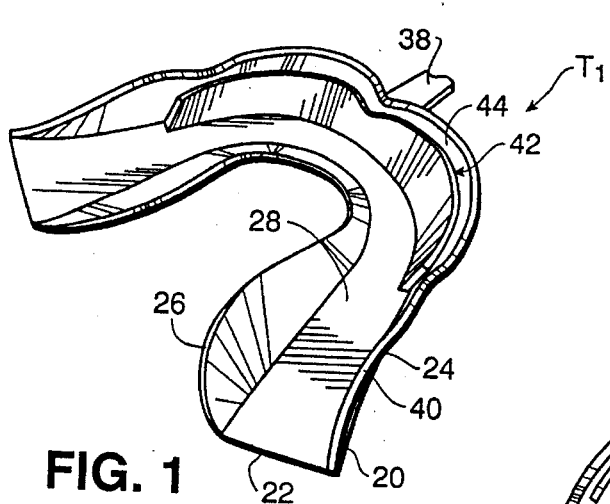
FIG. 1 is a perspective view of a tray constructed in accordance with and embodying the present invention.
Figure 2:
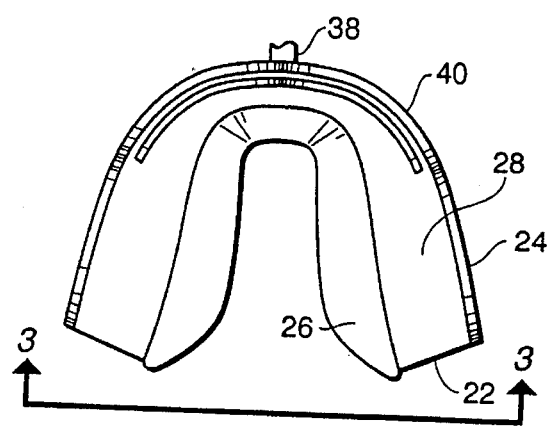
FIG. 2 is a top plan view the tray of FIG. 1.
Figure 3:
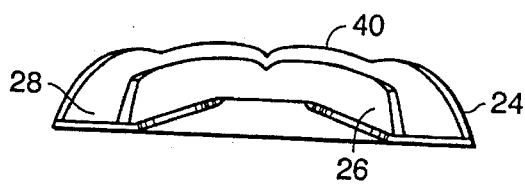
FIG. 3 is an end elevational view of the tray taken substantially along the plane of line 3—3 of FIG. 2.

Referring now in more detail and by reference characters to the drawings which will illustrate several practical embodiments of the present invention, $T_1$ designates a tray constructed in accordance with the present invention which may be used for applying a bleaching agent to teeth. The tray $T_1$ generally comprises an arch configured U-shaped trough forming member 20, having a bottom wall 22 and a somewhat arch-shaped exterior wall 24 integral therewith and a somewhat arch-shaped interior wall 26, also integral therewith. It can be seen that the two walls 24 and 26 are spaced from each other to form an interior channel or groove or so-called "trough" 28 sized receive the teeth of the user.

The tray $T_1$ of the present invention is preferably formed of any of a number of plastic materials which are capable of being molded when heated. A vinyl plastic is one of the preferred materials since it can be heated and becomes pliable and moldable at a relatively low temperature, although the invention is clearly not limited to the use of vinyl plastics. Other plastic materials, such as styrene copolymers and the like, could also be used.

The tray $T_1$ is provided on its exterior surface with a handle 38 for engagement by the user. This handle is preferably integral with the exterior wall 24 and would extend outwardly between the lips of the user when the arch is disposed about the teeth of the user.

The upper edge 40 of the exterior wall may be scalloped, that is, provided with a somewhat serpentine edge portion, as shown. In this way, the outer wall will more fully conform to the roof portion of the mouth existing between the teeth and the lips of the user.

An arch-shaped insert 42 is also located in the channel 28 and essentially has an arch shape similar to that of the exterior wall. Moreover, the insert 42 is slightly spaced inwardly from the interior surface of the exterior wall 24 so as to form a reservoir 44. In the embodiment of the invention as shown, the insert 42 does not extend for the full distance of the exterior wall 24 but does extend around a substantial portion of the arch to particularly span those teeth which are visible during a smile or conversation of a user.

Figure 4:
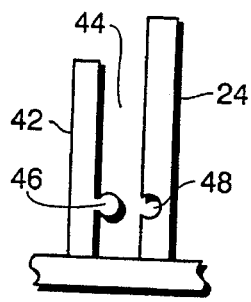
FIG. 4 is a fragmentary end elevational view showing a means for attachment of an insert to a wall of the tray.

The insert 42 may be removably held in position to form the reservoir 44 by means of tabs 46 formed along the lower edge of the insert 42 and which extend into detents or depressions 48 formed on the interior surface of the exterior wall 24, as best shown in FIG. 4 of the drawings. However, any means for temporarily retaining the insert in the position in the tray may be used.

In order to form the tray and effectively mold the same to conform to the shape of the user's arch and teeth, the plastic forming the tray, and the liner is heated so as to become somewhat flexible and pliable, that is effectively moldable. Heating may be accomplished in any of a variety of ways. A typically convenient way is to insert the tray into a bath of hot water. The tray can be merely dipped into the water by holding the outer end of the handle 30. Thereafter, the tray is placed on the teeth of the user and allowed to effectively conform to the shape of the user's teeth. A simple tapping or pressing on the inner and outer surfaces of the tray and particularly the walls 24 and 26, will cause the tray to effectively conform to the shape of the user's teeth and arch.

After the tray has been removed from the user's mouth, it is again heated, typically by the same means, for example, introducing the same into a bath of hot water momentarily. The tray is then allowed to cool. In its cooled configuration, the tray effectively is a mirror image of the teeth and both the inner and outer surfaces thereof. Thus, the tray constitutes an effective mold of the user's teeth. Generally, one tray would be used for the upper teeth and another tray would be used for the lower set of teeth.

Figure 5:
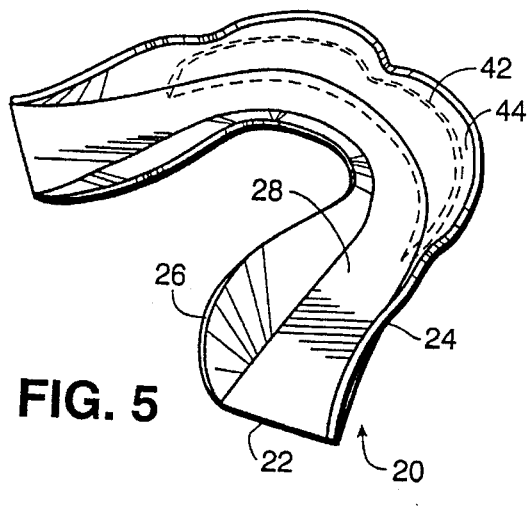
FIG. 5 is a perspective view of the tray of FIGS. 1–4 when the insert has been removed.
Figure 6:
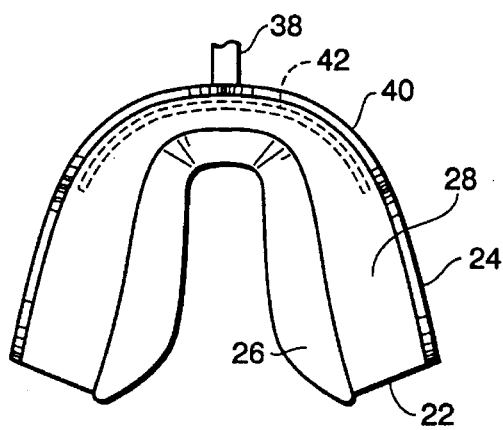
FIG. 6 is a top plan view of the tray of FIGS. 1–4 with the insert removed.

After the tray has been cooled, the insert 42 is removed, which leaves the tray as best shown in FIGS. 5 and 6 of the drawings. In this case, it can be seen that the position of the insert which has now been removed, is shown in the dotted lines. Thus, there is an additional space between the front surface of the teeth and the interior surface of the exterior wall 24 and that space is effectively the reservoir 44.

The insert 42 is of a relatively then cross-sectional shape and typically is of the order of one-half millimeter in thickness. However, any reasonably sized insert may be used for this purpose. Moreover, the insert 42 is preferably made of the same material used in the formation of the tray $T_1$.

The gel which may be used in the brightening operation is conventional. Any of the gels now in use and previously used for brightening of teeth may also be employed with the tray of the instant application.

Figure 7:
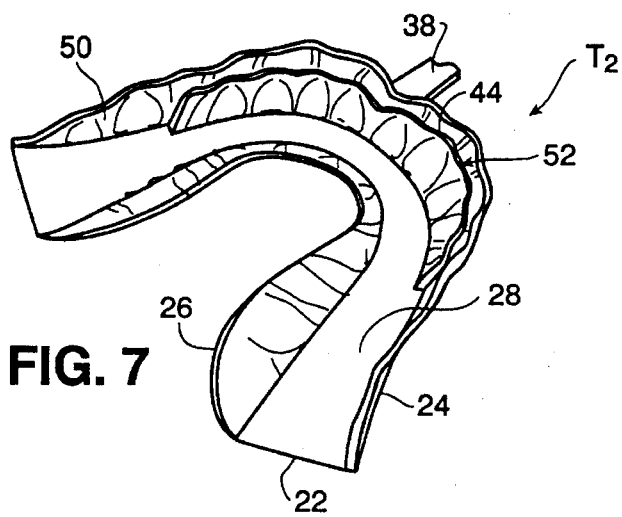
FIG. 7 is a perspective view of a modified form of tray constructed in accordance with and embodying the prevent invention.
Figure 8:
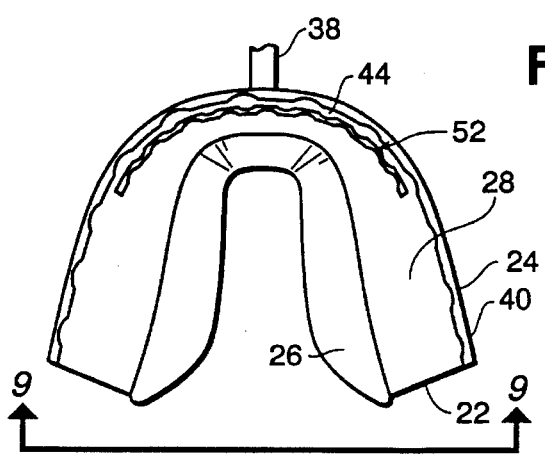
FIG. 8 is a top plan view of the tray of FIG. 7.
Figure 9:
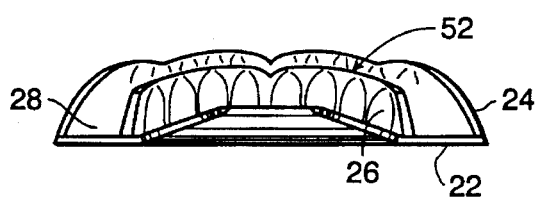
FIG. 9 is an end elevational view of the tray of FIGS. 7 and 8 taken substantially along the plane of line 9–9 of FIG. 8.

FIGS. 7–9 of the drawings illustrate a slightly modified form of tray $T_2$ and which is similar to the tray $T_1$. The tray $T_2$ is also provided on the interior surface of the exterior wall 24 with a somewhat scalloped surface configuration 50 as shown. Moreover, a modified form of insert 52 is used in the embodiment of the invention $T_2$. In this case, the overall insert 52 has somewhat of a serpentine shape or so-called "scalloped shape", as best illustrated in FIGS. 7–9 of the drawings. The serpentine or undulating surface of the insert 52 effectively conforms to the undulating interior surface 50 of the exterior wall 24.

In accordance with the construction as illustrated in FIGS. 7–9, it can be seen that the tray $T_2$ more accurately conforms to and fits the teeth shape of the user. Beyond this, the tray $T_1$ is similar to the tray $T_1$ in overall construction. Moreover, the tray $T_1$ is used in essentially the same manner as the tray $T_1$.

Figure 10:
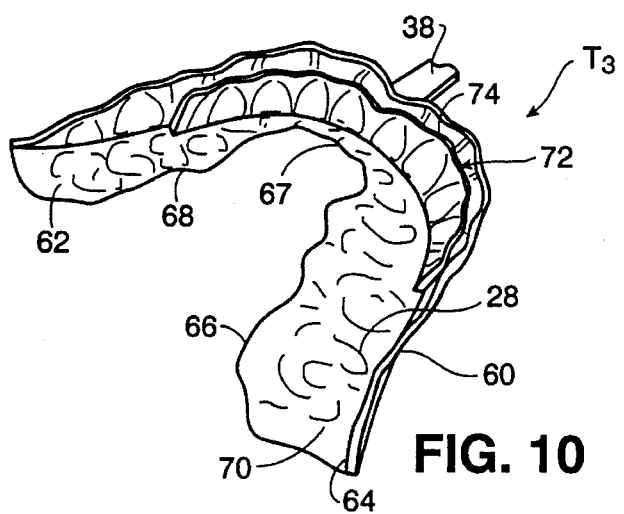
FIG. 10 is a perspective view of still another modified form of tray constructed in accordance with and embodying the present invention.

FIG. 10 illustrates a further modified form of tray, $T_3$ which is also constructed in accordance with and embodies the present invention. The tray $T_3$ differs from the previously described trays $T_1$ and $T_2$ in that it is somewhat V-shaped in cross-section, as opposed to U-shaped in cross-section, as shown, for example, in FIGS. 1 and 3 and 5, 6, 7 and 8 of the drawings. In this case, the tray $T_3$ is comprised of an outer wall 60 and an inner wall 62, which somewhat merges into a lower end 64, as best illustrated. In effect, the inner wall 62 actually forms a pair of flaps 66 and 68 which lie against the upper surface of the roof of the mouth. Nevertheless, even in the V-shaped configuration, the two walls 60 and 62 do form an interior channel 70 for receiving the teeth of the user.

The walls 60 and 62 may also be scalloped much in the same manner as the walls shown in the embodiment $T_2$ in FIGS. 7–9 of the drawings. The tray $T_1$ is further provided with an insert 72 and which is similarly spaced rearwardly of the interior surface of the outer wall 60 thereby forming a reservoir 74. The reservoir again is similar to the reservoir 44 in the trays $T_1$ and $T_2$. Thus, it can be seen that the tray $T_1$ operates much in the same manner as the trays $T_1$ and $T_2$.

In use, the tray $T_1$ would be employed much in the same manner as the trays $T_1$ and $T_2$. In this case, the insert $7_2$ is removed after the molding operation such that the tray then conforms to the configuration of the teeth and the arch of the user. Thereafter, the tray is used with a gel bleaching agent much in the same manner as used in the trays $T_1$ and $T_2$.

Thus, there has been illustrated and described a unique and novel applicator for applying a bleaching agent to the teeth of a user and a method of making the applicator and a method of using the applicator. The present invention therefore fulfills all of the objects and advantages which have been sought. It should be understood that many changes, modifications, variations and other uses and applications will become apparent to those skilled in the art after considering this specification and the accompanying drawings. Therefore, any and all such changes, modifications, variations and other uses and applications which do not depart from the spirit and scope of the invention are deemed to be covered by the invention.

Having thus described the invention, what I desire to claim and secure by letters patent is:

1. A bleaching tray for applying a bleaching composition to the teeth of a user, said tray comprising:

a) an arch-shaped outer wall adapted to extend around the exterior surface of the teeth of a user in the arch of the user;

b) an arch-shaped inner wall connected to said outer wall and adapted to extend around and substantially engage the interior surface of the teeth in the arch of the user; and c) said inner and outer walls being sized and shaped to form a recess which receives and substantially engages and retentively holds the tray when in use on the arch of the user, the interior surface of said outer wall being slightly spaced from the exterior surface of the teeth in the frontal portion of the arch;

d) said tray being formed of a flexible and pliable plastic material which is capable of being molded; and e) an insert removably located in said recess and which has an upstanding insert wall spaced apart from an inner surface of the outer wall by a small distance to define a bleaching agent receiving reservoir when removed, said insert being present in said recess when the tray is fitted to a user and removed thereafter so that when used on a user with a bleaching composition the interior surface of the outer wall is spaced from the exterior surface of the teeth in the frontal portion of the arch, such that the bleaching agent receiving reservoir around the front of the teeth allows the bleaching agent introduced into the reservoir to be in contact with the teeth.

2. The tray of claim 1 further characterized in that said tray extends around the frontal portion and a portion of the sides of the user's arch when in use.

3. The tray of claim 1 further characterized in that the interior surface of the outer wall and the exterior surface of the inner wall are relatively smooth.

4. The tray of claim 1 further characterized in that the interior surface of the outer wall and the exterior surface of the inner wall have somewhat of a serpentine configuration.

5. The tray of claim 1 further characterized in that said tray has a U-shaped configuration in cross-section.

6. The tray of claim 1 further characterized in that said tray has somewhat of a V-shaped configuration in cross-section.

7. The tray of claim 1 further characterized in that the tray is formed of a moldable plastic material and the insert is formed of a moldable plastic material which are heated to be shaped to the arch of the user and cooled to provide a set thereto and so that the insert can then be removed.

8. The tray of claim 7 further characterized in that the moldable plastic material is one which can be softened for molding by heating in a bath of hot water.

9. A tray assembly used in the formation of a tray for applying a bleaching agent to the teeth of a user, said tray assembly comprising:

a) a somewhat arch-shaped outer wall generally conforming to the shape of the teeth in the arch of the user's mouth;

b) an inner wall connected to said outer wall and also being of an arch shape and generally conforming to the shape of the teeth in the arch of the user;

c) a removable insert located in said tray assembly and having an upstanding insert wall positioned between an interior surface of the said outer wall and an exterior surface of said inner wall;

d) means releasably retaining said insert with the insert wall in a spaced apart relationship with respect to said outer wall to thereby form a reservoir existing between the interior surface of the outer wall and an exterior surface of said insert wall; and e) said tray assembly including the outer and inner walls and the insert being formed of a plastic material which is capable of being effectively molded to conform to the shape and contour of the user's teeth in an arch and upon removing the insert said reservoir is formed in the frontal portion thereof between the inner surface of the outer wall and the outer surface of the user's teeth to receive a bleaching agent so that when the insert is removed the reservoir thereby allows the front surface of the teeth to be held in contact with the bleaching agent.

10. The tray assembly of claim 9 further characterized in that said tray is adapted to extend around the frontal portion and a portion of the sides of the user's arch.

11. The tray assembly of claim 9 further characterized in that said plastic material used in said tray is a flexible and pliable plastic material.

12. The tray assembly of claim 9 further characterized in that the interior surface of the outer wall and the exterior surface of the inner wall are relatively smooth.

13. The tray assembly of claim 9 further characterized in that the interior surface of the outer wall and the exterior surface of the inner wall have somewhat of a serpentine configuration.

14. The tray assembly of claim 9 further characterized in that said tray has a U-shaped configuration in cross-section.

15. The tray assembly of claim 9 further characterized in that said tray has somewhat of a V-shaped configuration in cross-section.

16. A method of making a tray for use in the application of a bleaching agent to the teeth of a user on a home-use basis, said method comprising:

a) heating a tray formed of a moldable plastic material so that the material forming the tray becomes somewhat pliable and bendable, and which tray is comprised of a front wall and a back wall connected together in the shape of an arch to conform to the arch shape of the user's teeth;

b) simultaneously with the heating of said tray, heating an insert located in said tray in a position spaced apart from an interior surface of said front wall and similarly causing the insert to become moldable, said insert being formed of a moldable material so as to become bendable and pliable when heated;

c) inserting said tray on the teeth of a user in the user's mouth and allowing the tray to become effectively molded to conform to the shape and contour of the user's teeth;

d) removing the tray from its position in the user's mouth and allowing the tray to cool to thereby form a mold effectively conforming to the overall shape and contour of the user's mouth and with a reservoir existing between the exterior face of the teeth in a smiling zone and the interior surface of the outer wall of the tray.

17. The method of claim 16 further characterized in that said method comprises releasably attaching the insert to the tray before the molding thereof.

18. The method of claim 16 further characterized in that said method comprises pushing portions of the tray against the teeth of the user while in the user's mouth in a molding stage so as to cause the tray to effectively conform to the shape and contour of the user's teeth.

19. The method of claim 16 further characterized in that said method comprises reheating the tray after removing the same from the user's mouth in the molding stage and thereafter cooling the tray.

20. A method of bleaching the teeth in a user's mouth with a bleaching tray on a home-use basis, said method comprising:

a) locating an insert in a tray having a trough forming a recess therein to fit around and receive the teeth in the arch of a user's mouth and causing the insert to be located in front of the front surface of the user's teeth;

b) causing the tray and the insert to effectively mold to the shape and contour of the user's teeth while in the mouth of the user;

c) removing the insert in the tray after the heating thereof to form a reservoir which exists between the exterior surface of the teeth and the interior surface of the outer wall of the tray;

d) introducing a bleaching agent into the reservoir of the tray; and e) placing the tray back on the teeth of the user in the arch in the user's mouth and allowing the bleaching agent to bleach the teeth of the user.

21. The method of claim 20 further characterized in that said method comprises molding the tray to conform to the shape and contour of the user's teeth by heating the same before inserting in the user's mouth and allowing the tray to conform to the shape and contour of the teeth in the user's mouth and thereafter removing the tray with the insert and allowing same to cool.

22. The method of claim 20 further characterized in that said method comprises pressing portions of the tray against the teeth in the user's mouth during the molding thereof.

23. A method of making a tray for use in the application of a bleaching agent to the teeth of a user on a home-use basis, said method comprising:

a) heating a tray formed of a moldable plastic material so that the material forming the tray becomes somewhat pliable and bendable, and which tray is comprised of a front wall and a back wall connected together in the shape of an arch to conform to the arch shape of the user's teeth;

b) simultaneously with the heating of said tray, heating an insert located in said tray in a position spaced apart from an interior surface of said front wall and similarly causing the insert to become moldable, said insert being formed of a moldable material so as to become bendable and pliable when heated;

c) inserting said tray on the teeth of a user in the user's mouth and allowing the tray to become effectively molded to conform to the shape and contour of the user's teeth;

d) removing the tray from its position in the user's mouth and allowing the tray to cool to thereby form a mold effectively conforming to the overall shape and contour of the user's mouth and upon removal of the insert from the tray forming a reservoir between the exterior face of the teeth in a smiling zone and the interior surface of the outer wall of the tray so that a bleaching agent in the reservoir will come into contact with the user's teeth.

24. The method of claim 23 further characterized in that said method comprises pushing portions of the tray against the teeth of the user while in the user's mouth in a molding stage with the insert in the tray so as to cause the tray to effectively conform to the shape and contour of the user's teeth and also form a reservoir therein.

25. The method of claim 24 further characterized in that said method comprises inserting the tray into a cooling bath after removing the same from the user's mouth in the molding stage to achieve the cooling of the tray.

26. A method of bleaching the teeth in a user's mouth with a bleaching tray on a home-use basis, said method comprising:

a) locating an insert in a tray having a trough forming a recess therein to fit around and receive the teeth in the arch of a user's mouth and causing the insert to be located in front of the front surface of the user's teeth;

b) causing the tray and the insert to effectively mold to the shape and contour of the user's teeth while in the mouth of the user;

c) cooling the tray after removal from the user's mouth to cause a setting of the tray with the shape and contour of the user's teeth;

d) removing the insert in the tray to form a reservoir which exists between the exterior surface of the teeth and the interior surface of the outer wall of the tray;

e) introducing a bleaching agent into the reservoir thus formed in the tray; and f) placing the tray without the insert back on the teeth of the user in the arch in the user's mouth and allowing the bleaching agent to bleach the teeth of the user.

27. The method of claim 26 further characterized in that said method comprises pressing portions of the tray against the teeth in the user's mouth during the molding thereof.

28. The tray of claim 27 further characterized in that the tray and the insert are formed of a moldable plastic material which is cooled after removal from the user's mouth to provide a set thereto by introduction into a cooling medium.

29. The tray of claim 28 further characterized in that the cooling medium is a bath of cold water.

* * * * *